(12) United States Patent
Xu et al.

(10) Patent No.: US 8,455,643 B2
(45) Date of Patent: Jun. 4, 2013

(54) 8-HYDROXYQUINOLINE-BASED WHITE-LIGHT-EMITTING ORGANIC ELECTROLUMINESCENT MATERIAL

(75) Inventors: Bingshe Xu, Taiyuan (CN); Hua Wang, Taiyuan (CN); Fangfang Wei, Taiyuan (CN); Huixia Xu, Taiyuan (CN); Xiaohong Fang, Taiyuan (CN); Yuying Hao, Taiyuan (CN); Liuqing Chen, Taiyuan (CN)

(73) Assignee: Taiyuan University of Technology, Shanxi (CN)

( * ) Notice: Subject to any disclaimer, the term of this patent is extended or adjusted under 35 U.S.C. 154(b) by 201 days.

(21) Appl. No.: 13/001,151

(22) PCT Filed: Sep. 7, 2009

(86) PCT No.: PCT/CN2009/073796
§ 371 (c)(1),
(2), (4) Date: Apr. 26, 2011

(87) PCT Pub. No.: WO2010/078762
PCT Pub. Date: Jul. 15, 2010

(65) Prior Publication Data
US 2011/0263856 A1    Oct. 27, 2011

(30) Foreign Application Priority Data
Jan. 12, 2009   (CN) .......................... 2009 1 0073653

(51) Int. Cl.
*C07F 3/06*   (2006.01)
*H01L 51/50*   (2006.01)

(52) U.S. Cl.
USPC .............................. 546/10; 313/504; 428/690

(58) Field of Classification Search
USPC .............................. 546/10; 313/504; 428/690
See application file for complete search history.

(56) References Cited

U.S. PATENT DOCUMENTS

| 4,720,432 | A | 1/1988 | VanSlkye et al. |
| 2006/0003184 | A1 | 1/2006 | Hatwar et al. |
| 2007/0115221 | A1 | 5/2007 | Buchhauser et al. |

FOREIGN PATENT DOCUMENTS

| CN | 1852933 | 10/2006 |
| CN | 101041667 | 9/2007 |
| CN | 101463253 | 6/2009 |
| CN | 101468966 | 7/2009 |
| JP | 2001213866 | 8/2001 |
| JP | 2001326080 | 11/2001 |

OTHER PUBLICATIONS

Ouyang, X. et al.: Design and synthesis of 2-substituted-8-hydroxyquinline zinc complexes with hole-transporting ability for highly effective yellow-light emitters. J. of Organomett. Chem., vol. 694, pp. 3511-3517, 2009.*
International Search Report for International Application No. PCT/CN2009/073796 issued by the Chinese Patent Office, mailed on Dec. 17, 2009.

* cited by examiner

*Primary Examiner* — Charanjit Aulakh
(74) *Attorney, Agent, or Firm* — RatnerPrestia (57) ABSTRACT

A white-light organic electroluminescent material based on 8-hydroxyquinoline and the method for preparing the same, as well as an organic light emitting diode including this material. The material may be the compound represented by the Formula (IX) having a DCDC group, a 5-position substituted 8-hydroxyquinolinyl group and a carbazolyl group as red light-, green light- and blue-light emitting groups, respectively. It exhibits a spectrum having a band width of 182.4 nm that substantially covers the visible-light region, and has a color coordinate of (0.3177, 0.3946), which just locates within the white-light area. Such a material is capable of realizing a white-light emission, and may be used in a white-light OLED as a single light-emitting layer, which can decrease the number of layers of the white-light OLED and thereby improve the luminous efficiency, stabilize the light color, lower the turn-on voltage and simplify the fabrication process.

15 Claims, 2 Drawing Sheets

8-HYDROXYQUINOLINE-BASED WHITE-LIGHT-EMITTING ORGANIC ELECTROLUMINESCENT MATERIAL

CROSS-REFERENCE TO RELATED APPLICATIONS

This application is a U.S. National Phase Application of PCT International Application PCT/CN2009/073796, filed Sep. 7, 2009, which claims priority from Chinese Application 200910073653.1, filed Jan. 12, 2009, the contents of each of which are incorporated herein by reference in their entirety for all purposes.

TECHNICAL FIELD

The invention relates to a white-light organic electroluminescent material and the method for preparing the same. More particularly, the invention relates to a white-light organic electroluminescent material derived from 8-hydroxyquinoline and the method for preparing the same. The invention also relates to an organic light emitting diode comprising a light-emitting layer formed of this material.

BACKGROUND

The organic light emitting diode (OLED) is a novel flat plate display device, which exhibits such performances as energy-saving, high response speed, high color stability, strong adaptability of environment, non-radiation, long lifetime, light weight, thin thickness, and so on. The research on OLED originated in the mid 1980s. For instance, the U.S. Pat. No. 4,720,432 disclosed an OLED which uses aromatic tertiary amine as the hole-transporting material and 8-Hydroxyquinoline aluminum as the light-emitting material, and which demonstrated a wide application prospect in the field of display.

Realization of a flat plate display with full-color, large size and huge information storage is one of the most vital goals of the development of OLED. Presently, the color display of OLED is mainly realized by the method of paralleling three color pixels of red, green and blue (i.e., RGB) or the method of stacking three color pixels. Although full-color OLED products based on the above methods have been on market, their fabrication processes are very complicated owing to strictly precise photoengraving and masking technologies during fabrication process, which limits the application and development of OLED.

Accordingly, more attention has been paid on the study of on full-color OLED color filter technology applying directly liquid crystal display (LCD) on white-light OLED to realize OLED full-color light emitting. This method exhibits such characteristics as simple production process and low production costs, and is in favor of commercialization of full-color OLED flat plate display. For example, the U.S. Patent Application Publication No. 2007/0115221A1 has disclosed a full-color OLED display applying the color filter technology and white-light OLED material.

The white-light OLED has a brightness of above 10,000 $cd/m^2$, a luminous efficiency of above 40 lm/W, a turn-on voltage of less than 4 V and a lifetime of above 20,000 hours (at the brightness of 800-1,000 $cd/m^2$). It characteristics of energy-saving, light weight and thin thickness indicate that it can be used not only as back lighting source of flat plate display, such as, liquid crystal display (LCD), but as a novel energy saving planar illuminating device to be used widely.

However, the prior art white-light OLED mainly suffers from the following problems: the luminous efficiency of the white-light OLED is still low, resulting in a low luminous efficiency of the device far lower than the practical standard of 50-80 lm/W, which does not meet the requirement for illumination; the color coordinate of white-light OLED is unstable due to the imbalance of injection of electrons and holes in it, which causes that the lighting color varies with the voltage; the lifetime of white-light OLED is still short, and is far less than the standard for lamination lifetime of 50000 hours; the production process of white-light OLED is relatively complicated, and both the material preparation process and device fabrication process need to be simplified to reduce its production costs.

In order to resolve the above problems, many device structure have been developed to meet the practical requirements of white-light OLED. For example, the U.S. Patent Application Publication No. US2006/0003184 has disclosed a white-light OLED comprising a first light-emitting layer and a second light-emitting layer. Although the device performance may be improved greatly, the fabrication process is complicated owing to great number of layers of the white-light OLED, and the device has a relative higher turn-on voltage and a relatively lower luminous efficiency. These problems may be resolved by employing a doping structure with a single light-emitting layer. However, it is difficult to precisely quantify the doping concentration of dyes. Moreover, the phase separation and interface degradation caused by the doping will shorten the lifetime of the device. Therefore, the optimal method to resolve the above problems is to prepare an ideal white-light organic electroluminescent, and to fabricate a single light-emitting layer by using it in white-light OLED. It will not only increase the luminous efficiency of the device, but can greatly simplify the fabrication process and reduce the production costs.

The white-light organic electroluminescent polymer (WOEP) is the most representative type of the prior art white-light electroluminescent materials. Such a material can be classified into three types of straight chain structure, branched chain structure and dendrite structure in its structure. For example, the Chinese Patent Application Publication No. 1852933A has disclosed a WOEP incorporating blue-light emitting repeating units and red-light emitting repeating units, or incorporating blue-light emitting repeating units, green-light emitting repeating units and red-light emitting repeating units. Among them, red-light emitting groups and green-light emitting groups can be inserted into the main chain of polyfluorene to realize the white-light emitting.

Alternatively, green-light emitting pendant groups and red-light emitting pendant groups can be connected with the main chain of polyfluorene to realize the white-light emitting. In the prior art, the WOEP emits white-light by the energy transmission between light-emitting groups with a wide bandgap and light-emitting groups with a narrow bandgap. This can be utilized to fabricate a white-light OLED with a single light-emitting layer so as to resolve the problems of the prior art white-light OLEDs having a relatively multilayered structure.

However, the fluorescence quantum efficiency is relatively low (below 0.1 in general), and need to be further improved if the WOEP is used as the light-emitting layer in the OLED, which is due to the strong molecule stacking effect among adjacent chains and the fluorescence quenching effect. The white-light WOEP can readily crystallize when it is used as the light-emitting layer in the white-light OLED owing to its low glass transition temperature (below 100° C. in general) and poor thermal stability. Further, the ratio of respective light-emitting groups needs to be precisely controlled in an order of magnitude of $10^{-4}$ during synthesis of the WOEP, which greatly increases difficulty of the synthesis. Furthermore, the WOEP is difficult to be purified in a desirable purity, and it is not in favor of a mass production.

SUMMARY OF THE INVENTION

To resolve the above problems, the present invention provides a small molecule white-light organic electroluminescent material having yellowish green light emitting groups, blue light emitting groups and red light emitting groups at the same time, and the method for preparing the same. The present invention also provides an organic light emitting diode comprising a light-emitting layer formed of the above material.

The white-light organic electroluminescent material of the present invention may be represented by the following Formula (I):

wherein, M represents a divalent metal ion; A represents a group containing a 8-hydroxyquinolinyl group, in which the 8-hydroxyquinolinyl group can be substituted by an alkyl, alkoxyl or amino group at 2- or 7-position; B represents a carbazolyl group; C represents a group containing a 3,3-dicyanomethylene-1-cyclohexenyl group, in which the 3,3-dicyanomethylene-1-cyclohexenyl group can be substituted by an alkyl or aromatic group at 5-position; and each of $L_1$ and $L_2$ independently represents a saturated or unsaturated linking group having 2 to 8 carbon atoms.

The above mentioned alkyl group mainly means an alkyl group having 1 to 6 carbon atoms, such as, the methyl, ethyl, n-propyl, iso-propyl, butyl, pentyl or hexyl group. The above mentioned alkoxy groups mainly means an alkoxy group having 1 to 6 carbon atoms, such as, the methoxyl, ethoxyl, iso-propyloxyl or butoxyl group. The above mentioned aromatic groups mainly means an aromatic group having 6 to 10 carbon atoms, such as, the phenyl, benzyl, or phenylethyl groups.

The above mention amino group can be a substituted amino group in addition to the —$NH_2$ group, such as, the methyl amino, dimethyl amino, ethyl amino, methyl ethyl amino, propyl amino, or diethyl amino group.

In the Formula (I), M may represent a divalent metal ion that can be chelated with the 8-hydroxyquiolinyl group. For example, M can be a divalent earth metal ion or a divalent transition metal ion. Preferably, in the formula (I), M can represents $Mg^{2+}$, $Ca^{2+}$, $Ba^{2+}$, $Zn^{2+}$, $Cu^{2+}$, $Fe^{2+}$ and the like. More preferably, M represents $Zn^{2+}$.

Preferably, In the Formula (I), A represents the 8-hydroxyquinolinyl group, B represents the carbazolyl group, and C represents the 3,3-dicyanomethylene-5,5-dimethyl-cyclohexenyl group.

In the Formula (I), $L_1$ is a linking group which links the group A containing a 8-hydroxyquinolinyl group with the carbazolyl group B, and may be a saturated or unsaturated straight linking group having 2 to 8 carbon atoms. $L_2$ is a linking group which links the carbazolyl group B with the group C containing a 3,3-dicyanomethylene-1-cyclohexenyl group, and may be a saturated or unsaturated straight linking group having 2 to 8 carbon atoms. Preferably, $L_1$ and $L_2$ independently represent a saturated linking group having 2 to 8 carbon atoms, such as, —$CH_2CH_2$—, —$CH_2CH_2CH_2$—, —$CH_2CH_2CH_2CH_2$—, —$CH_2CH_2CH_2CH_2CH_2CH_2$—, —$CH_2CH_2CH_2CH_2CH_2CH_2CH_2CH_2$— and the like.

In the white-light organic electroluminescent material of the present invention represented by the Formula (I), the carbazolyl group B is linked with the group A containing a 8-hydroxyquinolinyl group. In this situation, the carbazolyl group B is linked with the group A containing a 8-hydroxyquinolinyl group at its 4- or 5-position through the linking group $L_1$.

In the white-light organic electroluminescent material of the present invention represented by the Formula (I), each of the carbazolyl group B can be linked with two groups C containing a 3,3-dicyanomethylene-1-cyclohexenyl group. In this situation, each of the two groups C containing a 3,3-dicyanomethylene-1-cyclohexenyl group is linked with the carbazolyl group B through the linking group $L_2$.

In a preferred embodiment, the organic electroluminescent material of the present invention is bi{5-{3,6-bis[2-(3,3-dicyanomethylene-5,5-dimethyl-cyclohexenyl)-ethenyl]-N-(6-hexyl)-carbazolyl}-8-hydroxyquinoline}zinc, (Zn$(C_{53}H_{49}N_6O)_2$, referred to as Zn(RCz-4CN-Q)$_2$ hereinafter) having a structure represented by the following Formula (IX):

(IX)

The method for preparing the white-light organic electroluminescent material of the present invention mainly comprises the following steps:

(i) coupling the carbazolyl group B with the linking group $L_1$ to obtain a compound represented by the Formula (II);

B-$L_1$ (II)

(ii) coupling the compound represented by the Formula (II) with the group C containing a 3,3-dicyanomethylene-1-cyclohexenyl group through a linking group $L_2$ to obtain a compound represented by the Formula (III);

C-$L_2$-B-$L_1$ (III)

(iii) coupling the compound represented by the Formula (III) with the group A containing a 8-hydroxyquinolinyl group to obtain a compound represented by the Formula (IV);

C-$L_2$-B-$L_1$-A (IV)

(iv) chelating the compound represented by the Formula (IV) with a divalent metal ion M to obtain the compound represented by the in Formula (I);

wherein, the M, A, B, C, $L_1$ and $L_2$ are defined the same as above.

In a preferred embodiment, the white-light organic electroluminescent material represented by the formula (IX) (Zn(RCz-4CN-Q)$_2$) can be prepared by a method comprising the following steps, as shown in Routine 1.

Routine 1

-continued (i-a) synthesizing N-(6-bromohexyl)-carbazole (BrRCz) from the starting material of carbazole and dibromohexane;

(i-b) preparing 3,6-diformyl-N-(6-bromohexyl)-carbazole (DFBrRCz) by reactiing BrRCz with $POCl_3$ and DMF;

(i-c) synthesizing 3,3-dicyanomethylene-5,5-dimethyl-cyclohexene (DCDC) by reacting isophorone with malononitrile; and synthesizing 3,6-bis[2-(3,3-dicyanomethylene-5,5-dimethyl-cyclohexenyl)-ethenyl]-N-(6-bromohexyl)-carbazole (BrRCz-4CN) by reacting DCM with DFBrRCz;

(ii-a) synthesizing 3,6-bis-[2-(3,3-dicyanomethylene-5,5-dimethyl-cyclohexenyl)-ethenyl]-N-[6-(4,4,5,5-tetramethyl-1,3,2-dioxaboran-2-yl)]-hexyl]-carbazole (BRCz-4CN) by reacting BrRCz-4CN with 2-isopropyl-4,4,5,5-tetramethyl-1,3,2-dioxa-borane;

(ii-b) synthesizing 5-{3,6-bis[2-(3,3-dicyanomethylene-5,5-dimethyl-cyclohexenyl)-ethenyl]-N-(6-hexyl)-carbazolyl}-8-hydroxyquinoline (RCz-4CN-Q) by reacting BRCz-4CN with 5-chloro-8-hydroxyquinoline;

(iii-c) synthesizing bi{5-{3,6-bis[2-(3,3-dicyanomethylene-5,5-dimethyl-cyclohexenyl)-ethenyl]-N-(6-hexyl)-carbazolyl}-8-hydroxyquinoline}zinc $(Zn(RCz-4CN-Q)_2)$ by adding zinc acetate in to RCz-4CN-Q.

In the present invention, the small molecule white-light organic electroluminescent material consists of a carbazolyl group as blue light emitting group, a 8-hydroxyquinolinyl group as green light emitting group and DCDC as red light emitting group. After being excited, the blue light emitting group emits blue light at first, where part of the blue light is used to induce the green light emitting group and the red light emitting group to emit light, and another part of the blue light is emitted out so as to combine with the green light and red light emitted from the green light emitting group and the red light emitting group, respectively, to realize a white-light emission. Such a material can be used in the white-light OLED as a single light-emitting layer, which can decrease the number of layers of the white-light OLED and thereby simplify the fabrication process of white-light OLED.

the small molecule white-light organic electroluminescent material of the present invention having the following features: 1) the molecular structure has a strong rigidity, and the conjugation between adjacent molecules is relative weak, which effectively avoids the fluorescence quenching, and provides this material a high fluorescence quantum efficiency; 2) it has a good solubility owing to its tridimensional molecular structure, which allows a film formation by means of vacuum evaporation as well as spin-coating or inkjet printing; 3) the molecular structure exhibits a totally non-planar spatial configuration with a relatively large steric hindrance, and the material can form a uniform amorphous thin film having a relatively high glass transition temperature which can effectively prolong the luminescent lifetime; 4) the material contains in the molecule carbazole groups having excellent hole-transporting performance and 8-hydroxyquinoline groups having excellent electron-transporting performance, which is in favor of balance of the transporting efficiency of electrons and holes, and thereby realize an effective combination of electrons and holes in the white-light OLED with a relatively high luminous efficiency. In conclusion, the small molecule white-light organic electroluminescent material of the present invention is a luminescent material having both high luminous efficiency and long lifetime.

Moreover, in preparation of the small molecule white-light organic electroluminescent material of the present invention, a white-light emission can be realized simply by a proper ratio of starting materials, which greatly reduces the synthetic difficulty, and is in favor of industrialized mass production.

DETAILED DESCRIPTION

Embodiments

Synthesis of White-light Organic Electroluminescent Material

Synthesis of $Zn(RCz-4CN-Q)_2$ $Zn(RCz-4CN-Q)_2$ was synthesized following the method depicted in Route 1. The details were as follows:

Under a nitrogen atmosphere, 1,6-dibromohexane was added into a solution of carbazole in tetrahydrofuran (THF), and then a potassium hydrate (KOH) solution was added dropwise during stirring in a molar ratio of carbazole:1,6~dibromohexane:KOH=1:1~3:3~10, where the amount of THF made up 25~35% of the total reaction system. The resultant mixture was reacted for 40~48 hours under reflux to synthesize the BrRCz.

Subsequently, BrRCz and N,N-dimethylformamide (DMF) were dissolved in 1,2-dichloroethane in a molar ratio of $BrRCz:DMF:POCl_3=1:2~3:2~3$, where the amount of DMF made up 80~90% of the total reaction system. $POCl_3$ was added into the resultant solution dropwise in an ice bath during stirring. The resultant reaction mixture was warmed slowly, and was reacted for 20~24 hours under reflux to synthesize DFBrRCz.

Molar equivalent isophorone and malononitrile were added into a mixed solution of glacial acetic acid, acetic anhydride, piperidine and DMF. The resultant mixture was reacted at room temperature for 1~2 hours, and then was warmed up to 70~90° C. and was further reacted for 1~2 hours. Thereafter, DFBrRCz is added in a molar ratio of DFBrRCz:isophorone malononitrile=1:2~8:2~8. The resultant mixture was further reacted for 1~2 hours at the temperature of 70~90° to synthersize BrRCz-4CN.

A BrRCz-4CN solution in THF was placed in a cooling bath of mixed liquid nitrogen/butanol solution, into which N-butyllithium was added under a nitrogen atmosphere in a molar ration of BrRCz-4CN:2-isopropyl-4,4,5,5-tetramethyl-1,3,2-dioxa-borane:N-butyllithium=1:1~2:1~2, where the amount of THF made up 90~95% of the total reaction system. After stirring for about 1 hour, 2-isopropyl-4,4,5,5-tetramethyl-1,3,2-dioxa-borane was quickly added. After further stirring for 2~3 hours, the mixture was warmed up to the room temperature, and further reacted for 20~26 hours to synthesize BRCz-4CN.

BRCz-4CN and 5-chloro-8-hydroxyquinoline were dissolved in ethylene glycol dimethyl ether in a molar ratio of 1:0.5~2 in the presence of the catalyst of $Pd(PPH_3)_4(0)$ in an amount of 1/3~1/6 based on the amount of BRCz-4CN, where the amount of ethylene glycol dimethyl ether made up 40~60% of the total reaction system. Equal volume (based on the volume of ethylene glycol dimethyl ether) of $Na_2CO_3$ aqueous solution (2 mol/L) was added into the resultant solution dropwise. The mixture was reacted for 20~26 hours under reflux to synthesize RCz-4CN-Q.

RCz-4CN-Q and zinc acetate were dissolved in anhydrous methanol in a molar ratio of 1~3:1. The resultant mixture was reacted for 3~5 hours under reflux to synthesize Zn(RCz-4CN-Q)$_2$.

Example 1

Carbazole (10 g) was added into THF (30 mL) in a 250 mL round bottom flask. After a complete dissolution, 1,6-dibromohexane (10 mL) was added. A KOH solution (12 mL, 16 mol/L) was then slowly added dropwise during stirring under nitrogen protection. Thereafter, the reaction solution was warmed to 80° C., and was reacted for 48 h under reflux. After completion of the reaction, the resultant mixture was distilled to remove the THF. The residue was extracted with deionized water (100 mL) and dichloromethane ($CH_2Cl_2$, 50 mL) for three times, respectively. The resultant organic layer was dried with anhydrous magnesium sulfate ($MgSO_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (3.8 mL) in 100 mL reaction flask, and then 1,2-dichloroethane (60 mL) was added. $POCl_3$ (7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (3.5 mL) and malononitrile (2.5 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 2 h at room temperature, was heated to 70° C., and then was further stirred for 1 h at this temperature. After adding-DFBrRCz (3 g), the reaction solution was further stirred for 2 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (1.3 mL) was added dropwise into the THF solution through a needle tube, and the resultant reaction solution was reacted for 2 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (0.32 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), $Pd(PPh_3)_4(O)$ (0.5 g) and 5-chloro-8-hydroxyquinoline (0.5 g) in ethylene glycol dimethyl ether (20 mL) was poured into a three-neck flask. A $Na_2CO_3$ solution (10 mL, 2 mol/L) was then slowly added dropwise. The reaction was carried out at a temperature of 80° C. for 25 hours. Thereafter, the reaction mixture was cooled to the room temperature, diluted with dichloromethane, and extracted with deionized water. The collected organic layer was washed with salt water, dried with anhydrous $MgSO_4$, and vacuum distilled to give the RCz-4CN-Q.

A solution obtained by dissolving RCz-4CN-Q (2 g) and zinc acetate (0.2 g) in anhydrous methanol (10 mL) was poured into flask. The temperature was adjusted to 80° C., and the reaction solution was reacted under this temperature for 5 hours. Thereafter, the resultant mixture was filtered. The obtained organic solution was collected and vacuum distilled. The residue was purified by silica column chromatography using petroleum ether as an eluent. The eluate was evaporated and vacuum dried to give the Zn(RCz-4CN-Q)$_2$.

IR spectrum (KBr pellet): ν=2968, 2223, 1652, 1600, 1386, 1555, 1105, 1084, 918, 771 $cm^{-1}$; $^1$H NMR (250 MHz, $CDCl_3$): δ=1.24, 1.43, 1.69, 1.77, 1.89, 3.42, 4.32, 6.52, 6.61, 7.25, 7.42, 8.01, 8.13, 8.59, 10.01 ppm.

Example 2

Carbazole (10 g) was added into THF (30 mL) in a 250 mL round bottom flask. After a complete dissolution, 1,6-dibromohexane (29 mL) was added. A KOH solution (37 mL, 16 mol/L) was then slowly added dropwise during stirring under nitrogen protection. Thereafter, the reaction solution was warmed to 80° C., and was reacted for 48 h under reflux. After completion of the reaction, the resultant mixture was distilled to remove the THF. The residue was extracted with deionized water (100 mL) and dichloromethane ($CH_2Cl_2$, 50 mL) for three times, respectively. The resultant organic layer was dried with anhydrous magnesium sulfate ($MgSO_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (5.7 mL) in 100 mL reaction flask, and then 1,2-dichloroethane (65 mL) was added. $POCl_3$ (7 mL) was added dropwise during stirring in an ice-water bath. Thereafter, the flask was placed in an oil bath. The reaction solution was slowly heated to 95° C., and then was further stirred for 20 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (2.3 mL) and malononitrile (3 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 2 h at room temperature, was heated to 80° C., and then was further stirred for 1 h at this temperature. After adding DFBrRCz (3 g), the reaction solution was further stirred for 1 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (1.3 mL) was added dropwise into the THF solution through a needle tube, and the resultant reaction solution was reacted for 2 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (1 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), $Pd(PPh_3)_4(O)$ (0.4 g) and 5-chloro-8-hydroxyquinoline (0.7 g) in ethylene glycol dimethyl ether (20 mL) was poured into a three-neck flask. A $Na_2CO_3$ solution (10 mL, 2 mol/L) was then slowly added dropwise. The reaction was carried out at a temperature of 80° C. for 24 hours. Thereafter, the reaction mixture was cooled to the room temperature, diluted with dichloromethane, and extracted with deionized water. The collected organic layer was washed with salt water, dried with anhydrous $MgSO_4$, and vacuum distilled to give the RCz-4CN-Q.

A solution obtained by dissolving RCz-4CN-Q (2 g) and zinc acetate (0.2 g) in anhydrous methanol (10 mL) was poured into flask. The temperature was adjusted to 80° C., and the reaction solution was reacted under this temperature for 5 hours. Thereafter, the resultant mixture was filtered. The obtained organic solution was collected and vacuum distilled. The residue was purified by silica column chromatography using petroleum ether as an eluent. The eluate was evaporated and vacuum dried to give the $Zn(RCz-4CN-Q)_2$.

IR spectrum (KBr pellet): ν=2967, 2223, 1654, 1598, 1386, 1555, 1104, 1084, 917, 769 $cm^{-1}$; $^1H$ NMR (250 MHz, $CDCl_3$): δ=1.25, 1.43, 1.70, 1.79, 1.89, 3.43, 4.32, 6.53, 6.61, 7.24, 7.43, 7.99, 8.14, 8.59, 10.00 ppm.

Example 3

Carbazole (10 g) was added into THF (30 mL) in a 250 mL round bottom flask. After a complete dissolution, 1,6-dibromohexane (29 mL) was added. A KOH solution (12 mL, 16 mol/L) was then slowly added dropwise during stirring under nitrogen protection. Thereafter, the reaction solution was warmed to 80° C., and was reacted for 48 h under reflux. After completion of the reaction, the resultant mixture was distilled to remove the THF. The residue was extracted with deionized water (100 mL) and dichloromethane ($CH_2Cl_2$, 50 mL) for three times, respectively. The resultant organic layer was dried with anhydrous magnesium sulfate ($MgSO_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (3.8 mL) in 100 mL reaction flask, and then 1,2-dichloroethane (60 mL) was added. $POCl_3$ (7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (2.3 mL) and malononitrile (1 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 1 h at room temperature, was heated to 90° C., and then was further stirred for 1 h at this temperature. After adding DFBrRCz (3 g), the reaction solution was further stirred for 1 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (0.4 mL) was added dropwise into the THF solution through a needle tube, and the resultant reaction solution was reacted for 3 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (1 g) was quickly added into the reaction solution immediately, and the resultant mixture was reacted for 26 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), $Pd(PPh_3)_4(O)$ (0.4 g) and 5-chloro-8-hydroxyquinoline (0.7 g) in ethylene glycol dimethyl ether (20 mL) was poured into a three-neck flask. A $Na_2CO_3$ solution (10 mL, 2 mol/L) was then slowly added dropwise. The reaction was carried out at a temperature of 80° C. for 20 hours. Thereafter, the reaction mixture was cooled to the room temperature, diluted with dichloromethane, and extracted with deionized water. The collected organic layer was washed with salt water, dried with anhydrous $MgSO_4$, and vacuum distilled to give the RCz-4CN-Q.

A solution obtained by dissolving RCz-4CN-Q (2 g) and zinc acetate (0.17 g) in anhydrous methanol (10 mL) was poured into flask. The temperature was adjusted to 80° C., and the reaction solution was reacted under this temperature for 4 hours. Thereafter, the resultant mixture was filtered. The obtained organic solution was collected and vacuum distilled. The residue was purified by silica column chromatography using petroleum ether as an eluent. The eluate was evaporated and vacuum dried to give the $Zn(RCz-4CN-Q)_2$.

IR spectrum (KBr pellet): ν=2968, 2221, 1650, 1602, 1384, 1557, 1105, 1083, 918, 771 $cm^{-1}$; $^1H$ NMR (250 MHz, $CDCl_3$): δ=1.24, 1.41, 1.68, 1.75, 1.90, 3.40, 4.31, 6.52, 6.60, 7.27, 7.42, 8.01, 8.13, 8.58, 10.01 ppm.

Example 4

Carbazole (10 g) was added into THF (30 mL) in a 250 mL round bottom flask. After a complete dissolution, 1,6-dibromohexane (19.44 mL) was added. A KOH solution (22.5 mL, 16 mol/L) was then slowly added dropwise during stirring under nitrogen protection. Thereafter, the reaction solution was warmed to 80° C., and was reacted for 40 h under reflux. After completion of the reaction, the resultant mixture was distilled to remove the THF. The residue was extracted with deionized water (100 mL) and dichloromethane ($CH_2Cl_2$, 50 mL) for three times, respectively. The resultant organic layer was dried with anhydrous magnesium sulfate ($MgSO_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (5.7 mL) in 100 mL reaction flask, and then 1,2-dichloroethane (65 mL) was added. $POCl_3$ (4.7 mL) was added dropwise during stirring in an ice-water bath. Thereafter, the flask was placed in an oil bath. The reaction solution was slowly heated to 95° C., and then was further stirred for 24 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (3.5 mL) and malononitrile (2.5 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 2 h at room temperature, was heated to 80° C., and then was further stirred for 1 h at this temperature. After adding DFBrRCz (3 g), the reaction solution was further stirred for 2 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (0.4 mL) was added dropwise into the THF solution through a needle tube, and the resultant reaction solution was reacted for 2 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (1 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), $Pd(PPh_3)_4(O)$ (0.5 g) and 5-chloro-8-hydroxyquinoline (0.5 g) in ethylene glycol dimethyl ether (20 mL) was poured into a three-neck flask. A $Na_2CO_3$ solution (10 mL, 2 mol/L) was then slowly added dropwise. The reaction was carried out at a temperature of 80° C. for 24 hours. Thereafter, the reaction mixture was cooled to the room temperature, diluted with dichloromethane, and extracted with deionized water. The collected organic layer was washed with salt water, dried with anhydrous $MgSO_4$, and vacuum distilled to give the RCz-4CN-Q.

A solution obtained by dissolving RCz-4CN-Q (2 g) and zinc acetate (0.2 g) in anhydrous methanol (10 mL) was poured into flask. The temperature was adjusted to 80° C., and the reaction solution was reacted under this temperature for 3 hours. Thereafter, the resultant mixture was filtered. The obtained organic solution was collected and vacuum distilled. The residue was purified by silica column chromatography using petroleum ether as an eluent. The eluate was evaporated and vacuum dried to give the $Zn(RCz-4CN-Q)_2$.

IR spectrum (KBr pellet): ν=2970, 2223, 1655, 1600, 1387, 1554, 1106, 1084, 918, 770 $cm^{-1}$; $^1H$ NMR (250 MHz, $CDCl_3$): δ=1.24, 1.43, 1.69, 1.77, 1.89, 3.42, 4.32, 6.52, 6.61, 7.24, 7.44, 8.01, 8.12, 8.59, 10.00 ppm.

Example 5

Carbazole (10 g) was added into THF (30 mL) in a 250 mL round bottom flask. After a complete dissolution, 1,6-dibromohexane (20 mL) was added. A KOH solution (20 mL, 16 mol/L) was then slowly added dropwise during stirring under nitrogen protection. Thereafter, the reaction solution was warmed to 90° C., and was reacted for 48 h under reflux. After completion of the reaction, the resultant mixture was distilled to remove the THF. The residue was extracted with deionized water (100 mL) and dichloromethane ($CH_2Cl_2$, 50 mL) for three times, respectively. The resultant organic layer was dried with anhydrous magnesium sulfate ($MgSO_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (3.8 mL) in 100 mL reaction flask, and then 1,2-dichloroethane (60 mL) was added. $POCl_3$ (7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (3.5 mL) and malononitrile (2.5 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 2 h at room temperature, was heated to 90° C., and then was further stirred for 2 h at this temperature. After adding DFBrRCz (3 g), the reaction solution was further stirred for 2 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (0.6 mL) was added dropwise into the THF solution through a needle tube, and the resultant reaction solution was reacted for 2 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (0.32 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), $Pd(PPh_3)_4(O)$ (0.5 g) and 5-chloro-8-hydroxyquinoline (1 g) in ethylene glycol dimethyl ether (20 mL) was poured into a three-neck flask. A $Na_2CO_3$ solution (10 mL, 2 mol/L) was then slowly added dropwise. The reaction was carried out at a temperature of 100° C. for 20 hours. Thereafter, the reaction mixture was cooled to the room temperature, diluted with dichloromethane, and extracted with deionized water. The collected organic layer was washed with salt water, dried with anhydrous $MgSO_4$, and vacuum distilled to give the RCz-4CN-Q.

A solution obtained by dissolving RCz-4CN-Q (2 g) and zinc acetate (0.13 g) in anhydrous methanol (10 mL) was poured into flask. The temperature was adjusted to 80° C., and the reaction solution was reacted under this temperature for 4 hours. Thereafter, the resultant mixture was filtered. The obtained organic solution was collected and vacuum distilled. The residue was purified by silica column chromatography using petroleum ether as an eluent. The eluate was evaporated and vacuum dried to give the $Zn(RCz-4CN-Q)_2$.

IR spectrum (KBr pellet): ν=2971, 2224, 1650, 1600, 1388, 1557, 1105, 1084, 918, 771 $cm^{-1}$; $^1H$ NMR (250 MHz, $CDCl_3$): δ=1.24, 1.43, 1.69, 1.78, 1.89, 3.41, 4.33, 6.53, 6.61, 7.25, 7.42, 8.01, 8.13, 8.59, 10.01 ppm.

Example 6

Carbazole (10 g) was added into THF (30 mL) in a 250 mL round bottom flask. After a complete dissolution, 1,6-dibromohexane (29 mL) was added. A KOH solution (22.5 mL, 16 mol/L) was then slowly added dropwise during stirring under nitrogen protection. Thereafter, the reaction solution was warmed to 80° C., and was reacted for 48 h under reflux. After completion of the reaction, the resultant mixture was distilled to remove the THF. The residue was extracted with deionized water (100 mL) and dichloromethane ($CH_2Cl_2$, 50 mL) for three times, respectively. The resultant organic layer was dried with anhydrous magnesium sulfate ($MgSO_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (3.8 mL) in 100 mL reaction flask, and then 1,2-dichloroethane (60 mL) was added. $POCl_3$ (7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (5.8 mL) and malononitrile (1.5 g) were added into a 100 mL reaction flask. A solution (9.6 mL) obtained by dissolving acetic acid (0.29 mL) and acetic anhydride (0.27 mL) in DMF (40 mL) and a solution (9.6 mL) obtained by dissolving piperidine (0.6 mL) in DMF (18 mL) were added into the reaction flask in sequence. The resultant reaction solution was stirred for 2 h at room temperature, was heated to 70° C., and then was further stirred for 2 h at this temperature. After adding DFBrRCz (3 g), the reaction solution was further stirred for 2 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (0.4 mL) was added dropwise into the THF solution through a needle tube, and the resultant reaction solution was reacted for 3 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (1 g) was quickly added into the reaction solution immediately, and the resultant mixture was reacted for 20 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), Pd(PPh$_3$)$_4$(O) (0.4 g) and 5-chloro-8-hydroxyquinoline (0.7 g) in ethylene glycol dimethyl ether (20 mL) was poured into a three-neck flask. A Na$_2$CO$_3$ solution (10 mL, 2 mol/L) was then slowly added dropwise. The reaction was carried out at a temperature of 80° C. for 24 hours. Thereafter, the reaction mixture was cooled to the room temperature, diluted with dichloromethane, and extracted with deionized water. The collected organic layer was washed with salt water, dried with anhydrous MgSO$_4$, and vacuum distilled to give the RCz-4CN-Q.

A solution obtained by dissolving RCz-4CN-Q (2 g) and zinc acetate (0.13 g) in anhydrous methanol (10 mL) was poured into flask. The temperature was adjusted to 80° C., and the reaction solution was reacted under this temperature for 5 hours. Thereafter, the resultant mixture was filtered. The obtained organic solution was collected and vacuum distilled. The residue was purified by silica column chromatography using petroleum ether as an eluent. The eluate was evaporated and vacuum dried to give the Zn(RCz-4CN-Q)$_2$.

IR spectrum (KBr pellet): ν=2966, 2224, 1652, 1600, 1388, 1557, 1104, 1084, 919, 771 cm$^{-1}$; $^1$H NMR (250 MHz, CDCl$_3$): δ=1.24, 1.42, 1.70, 1.79, 1.89, 3.43, 4.32, 6.53, 6.60, 7.26, 7.42, 8.00, 8.13, 8.59, 10.00 ppm.

Example 7

Carbazole (10 g) was added into THF (30 mL) in a 250 mL round bottom flask. After a complete dissolution, 1,6-dibromohexane (20 mL) was added. A KOH solution (32 mL, 16 mol/L) was then slowly added dropwise during stirring under nitrogen protection. Thereafter, the reaction solution was warmed to 90° C., and was reacted for 48 h under reflux. After completion of the reaction, the resultant mixture was distilled to remove the THF. The residue was extracted with deionized water (100 mL) and dichloromethane (CH$_2$Cl$_2$, 50 mL) for three times, respectively. The resultant organic layer was dried with anhydrous magnesium sulfate (MgSO$_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (3.8 mL) in 100 mL reaction flask, and then 1,2-dichloroethane (60 mL) was added. POCl$_3$ (4.7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (2.3 mL) and malononitrile (3 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 1 h at room temperature, was heated to 70° C., and then was further stirred for 2 h at this temperature. After adding. DFBrRCz (3 g), the reaction solution was further stirred for 1 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (0.6 mL) was added dropwise into the THF solution through a needle tube, and the resultant reaction solution was reacted for 3 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (0.32 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous MgSO$_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), Pd(PPh$_3$)$_4$(O) (0.5 g) and 5-chloro-8-hydroxyquinoline (1 g) in ethylene glycol dimethyl ether (20 mL) was poured into a three-neck flask. A Na$_2$CO$_3$ solution (10 mL, 2 mol/L) was then slowly added dropwise. The reaction was carried out at a temperature of 100° C. for 25 hours. Thereafter, the reaction mixture was cooled to the room temperature, diluted with dichloromethane, and extracted with deionized water. The collected organic layer was washed with salt water, dried with anhydrous MgSO$_4$, and vacuum distilled to give the RCz-4CN-Q.

A solution obtained by dissolving RCz-4CN-Q (2 g) and zinc acetate (0.2 g) in anhydrous methanol (10 mL) was poured into flask. The temperature was adjusted to 80° C., and the reaction solution was reacted under this temperature for 4 hours. Thereafter, the resultant mixture was filtered. The obtained organic solution was collected and vacuum distilled. The residue was purified by silica column chromatography using petroleum ether as an eluent. The eluate was evaporated and vacuum dried to give the Zn(RCz-4CN-Q)$_2$.

IR spectrum (KBr pellet): ν=2968, 2224, 1653, 1600, 1386, 1556, 1104, 1081, 916, 771 cm$^{-1}$; $^1$H NMR (250 MHz, CDCl$_3$): δ=1.24, 1.45, 1.69, 1.77, 1.90, 3.43, 4.32, 6.52, 6.59, 7.26, 7.42, 8.00, 8.13, 8.60, 10.00 ppm.

Example 8

Carbazole (10 g) was added into THF (30 mL) in a 250 mL round bottom flask. After a complete dissolution, 1,6-dibromohexane (29.2 mL) was added. A KOH solution (22.5 mL, 16 mol/L) was then slowly added dropwise during stirring under nitrogen protection. Thereafter, the reaction solution was warmed to 80° C., and was reacted for 40 h under reflux. After completion of the reaction, the resultant mixture was distilled to remove the THF. The residue was extracted with deionized water (100 mL) and dichloromethane (CH$_2$Cl$_2$, 50 mL) for three times, respectively. The resultant organic layer was dried with anhydrous magnesium sulfate (MgSO$_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (5.7 mL) in 100 mL reaction flask, and then 1,2-dichloroethane (65 mL) was added. POCl$_3$ (4.7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (3.5 mL) and malononitrile (2.5 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 2 h at room temperature, was heated to 80° C., and then was further stirred for 2 h at this temperature. After adding DFBrRCz (3 g), the reaction solution was further stirred for 2 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at –78° C. Under a nitrogen atmosphere, an n-butyllithium (0.6 mL) was added dropwise into the THF solution through a needle tube, and the resultant reaction solution was reacted for 3 hours. Thereafter, the reaction temperature was heated from –78° C. to 0° C. within 15 minutes, and then cooled to –78° C. over 15 minutes. A 2-isopropyl-4,4,5,5-tetramethyl-1,3,2-dioxaborane (0.32 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous MgSO$_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), Pd(PPh$_3$)$_4$(O) (0.5 g) and 5-chloro-8-hydroxyquinoline (0.13 g) in ethylene glycol dimethyl ether (20 mL) was poured into a three-neck flask. A Na$_2$CO$_3$. solution (10 mL, 2 mol/L) was then slowly added dropwise. The reaction was carried out at a temperature of 80° C. for 25 hours. Thereafter, the reaction mixture was cooled to the room temperature, diluted with dichloromethane, and extracted with deionized water. The collected organic layer was washed with salt water, dried with anhydrous MgSO$_4$, and vacuum distilled to give the RCz-4CN-Q.

A solution obtained by dissolving RCz-4CN-Q (2 g) and zinc acetate (0.2 g) in anhydrous methanol (10 mL) was poured into flask. The temperature was adjusted to 90° C., and the reaction solution was reacted under this temperature for 4 hours. Thereafter, the resultant mixture was filtered. The obtained organic solution was collected and vacuum distilled. The residue was purified by silica column chromatography using petroleum ether as an eluent. The eluate was evaporated and vacuum dried to give the Zn(RCz-4CN-Q)$_2$.

IR spectrum (KBr pellet): ν=2966, 2222, 1651, 1599, 1386, 1555, 1104, 1085, 920, 770 cm$^{-1}$; $^1$H NMR (250 MHz, CDCl$_3$): δ=1.26, 1.43, 1.69, 1.78, 1.88, 3.41, 4.33, 6.52, 6.60, 7.25, 7.42, 8.00, 8.12, 8.59, 10.00 ppm.

Example 9

Carbazole (10 g) was added into THF (30 mL) in a 250 mL round bottom flask. After a complete dissolution, 1,6-dibromohexane (29.2 mL) was added. A KOH solution (22.5 mL, 16 mol/L) was then slowly added dropwise during stirring under nitrogen protection. Thereafter, the reaction solution was warmed to 80° C., and was reacted for 48 h under reflux. After completion of the reaction, the resultant mixture was distilled to remove the THF. The residue was extracted with deionized water (100 mL) and dichloromethane (CH$_2$Cl$_2$, 50 mL) for three times, respectively. The resultant organic layer was dried with anhydrous magnesium sulfate (MgSO$_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (3.8 mL) in 100 mL reaction flask, and then 1,2-dichloroethane (60 mL) was added. POCl$_3$ (7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (2.3 mL) and malononitrile (1 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 1 h at room temperature, was heated to 80° C., and then was further stirred for 1 h at this temperature. After adding DFBrRCz (3 g), the reaction solution was further stirred for 1 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at –78° C. Under a nitrogen atmosphere, an n-butyllithium (0.4 mL) was added dropwise into the THF solution through a needle tube, and the resultant reaction solution was reacted for 2 hours. Thereafter, the reaction temperature was heated from –78° C. to 0° C. within 15 minutes, and then cooled to –78° C. over 15 minutes. A 2-isopropyl-4,4,5,5-tetramethyl-1,3,2-dioxaborane (1 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), $Pd(PPh_3)_4(O)$ (0.5 g) and 5-chloro-8-hydroxyquinoline (0.13 g) in ethylene glycol dimethyl ether (20 mL) was poured into a three-neck flask. A $Na_2CO_3$ solution (10 mL, 2 mol/L) was then slowly added dropwise. The reaction was carried out at a temperature of 80° C. for 25 hours. Thereafter, the reaction mixture was cooled to the room temperature, diluted with dichloromethane, and extracted with deionized water. The collected organic layer was washed with salt water, dried with anhydrous $MgSO_4$, and vacuum distilled to give the RCz-4CN-Q.

A solution obtained by dissolving RCz-4CN-Q (2 g) and zinc acetate (0.4 g) in anhydrous methanol (10 mL) was poured into flask. The temperature was adjusted to 90° C., and the reaction solution was reacted under this temperature for 5 hours. Thereafter, the resultant mixture was filtered. The obtained organic solution was collected and vacuum distilled. The residue was purified by silica column chromatography using petroleum ether as an eluent. The eluate was evaporated and vacuum dried to give the $Zn(RCz-4CN-Q)_2$.

IR spectrum (KBr pellet): ν=2966, 2225, 1652, 1599, 1387, 1555, 1104, 1086, 918, 770 $cm^{-1}$; $^1H$ NMR (250 MHz, $CDCl_3$): δ=1.25, 1.43, 1.69, 1.78, 1.89, 3.41, 4.33, 6.55, 6.63, 7.24, 7.43, 8.00, 8.14, 8.57, 9.99 ppm.

Example 10

Carbazole (10 g) was added into THF (30 mL) in a 250 mL round bottom flask. After a complete dissolution, 1,6-dibromohexane (29 mL) was added. A KOH solution (37 mL, 16 mol/L) was then slowly added dropwise during stirring under nitrogen protection. Thereafter, the reaction solution was warmed to 80° C., and was reacted for 40 h under reflux. After completion of the reaction, the resultant mixture was distilled to remove the THF. The residue was extracted with deionized water (100 mL) and dichloromethane ($CH_2Cl_2$, 50 mL) for three times, respectively. The resultant organic layer was dried with anhydrous magnesium sulfate ($MgSO_4$), and was concentrated to obtain a crude product. The crude product was purified by silica column chromatography using petroleum ether as an eluent. The eluate was evaporated and vacuum dried to give the BrRCz as a colorless crystal.

BrRCz (8 g) was weighed and added into DMF (3.8 mL) in 100 mL reaction flask, and then 1,2-dichloroethane (60 mL) was added. $POCl_3$ (7 mL) was added dropwise during stirring in an ice-water bath. Thereafter, the flask was placed in an oil bath. The reaction solution was slowly heated to 95° C., and then was further stirred for 21 h. After being cooled to 50° C., the reaction solution was poured into ice water (150 mL), into which an aqueous sodium hydroxide (NaOH) solution (1 mol/L) was added dropwise under stirring to adjust the pH value of the solution to 7. Thereafter, the solution was extracted with acetic ester, and the obtained organic layer was collected and concentrated. The residue was purified by silica column chromatography using methylbenzene/petroleum ether (8:5) as an eluent. The eluate was evaporated and vacuum dried to give the DFBrRCz.

Isophorone (2.3 mL) and malononitrile (0.5 g) were added into a 100 mL reaction flask. A solution (9.6 mL) obtained by dissolving acetic acid (0.32 mL) and acetic anhydride (0.24 mL) in DMF (40 mL) and a solution (9.6 mL) obtained by dissolving piperidine (0.8 mL) in DMF (20 mL) were added into the reaction flask in sequence. The resultant reaction solution was stirred for 2 h at room temperature, was heated to 90° C., and then was further stirred for 1 h at this temperature. After adding DFBrRCz (3 g), the reaction solution was further stirred for 1 h. The hot mixture solution was poured into hot water (200 mL) containing concentrated hydrochloric acid (6 mL) immediately to allow precipitation of solid. The precipitated solid was collected, washed with deionized water, vacuum filtered and recrystallized over acetonitrile to give BrRcZ-4CN.

The solution obtained by dissolving BrRCz-4CN (2 g) in THF (30 mL) was poured into a three-neck flask placed in a cooling bath of mixed liquid nitrogen/n-butanol at −78° C. Under a nitrogen atmosphere, an n-butyllithium (0.7 mL) was added dropwise into the THF solution through a needle tube, and the resultant reaction solution was reacted for 3 hours. Thereafter, the reaction temperature was heated from −78° C. to 0° C. within 15 minutes, and then cooled to −78° C. over 15 minutes. A 2-isopropyl-4,4,5,5-tetramethyl-1,3,2-dioxaborane (0.32 g) was quickly added into the reaction solution immediately, and the resultant mixture was reacted for 24 h at the room temperature. Thereafter, the resultant reaction mixture was poured into water, and was extracted with ether. The organic layer was collected, washed with salt water, dried with anhydrous $MgSO_4$. Solvents were removed under vacuum to give a pale yellow solid. The obtained solid was recrystallized over methanol/THF to give a solid as white powders, which is then purified by silica column chromatography using acetic ester/n-hexane as an eluent. The eluate was evaporated and vacuum dried to give the BRCz-4CN.

A solution obtained by dissolving BRCz-4CN (2 g), $Pd(PPh_3)_4(O)$ (0.5 g) and 5-chloro-8-hydroxyquinoline (0.5 g) in ethylene glycol dimethyl ether (20 mL) was poured into a three-neck flask. A $Na_2CO_3$ solution (10 mL, 2 mol/L) was then slowly added dropwise. The reaction was carried out at a temperature of 80° C. for 25 hours. Thereafter, the reaction mixture was cooled to the room temperature, diluted with dichloromethane, and extracted with deionized water. The collected organic layer was washed with salt water, dried with anhydrous $MgSO_4$, and vacuum distilled to give the RCz-4CN-Q.

A solution obtained by dissolving RCz-4CN-Q (2 g) and zinc acetate (0.2 g) in anhydrous methanol (10 mL) was poured into flask. The temperature was adjusted to 80° C., and the reaction solution was reacted under this temperature for 4 hours. Thereafter, the resultant mixture was filtered. The obtained organic solution was collected and vacuum distilled. The residue was purified by silica column chromatography using petroleum ether as an eluent. The eluate was evaporated and vacuum dried to give the $Zn(RCz-4CN-Q)_2$.

IR spectrum (KBr pellet): ν=2965, 2221, 1654, 1601, 1387, 1554, 1103, 1084, 919, 772 $cm^{-1}$; $^1H$ NMR (250 MHz, $CDCl_3$): δ=1.24, 1.45, 1.67, 1.79, 1.89, 3.44, 4.31, 6.52, 6.59, 7.24, 7.42, 8.02, 8.14, 8.59, 10.02 ppm.

Properties of White-Light Organic Electroluminescent Material

Fluorescence Property

Figure 1:
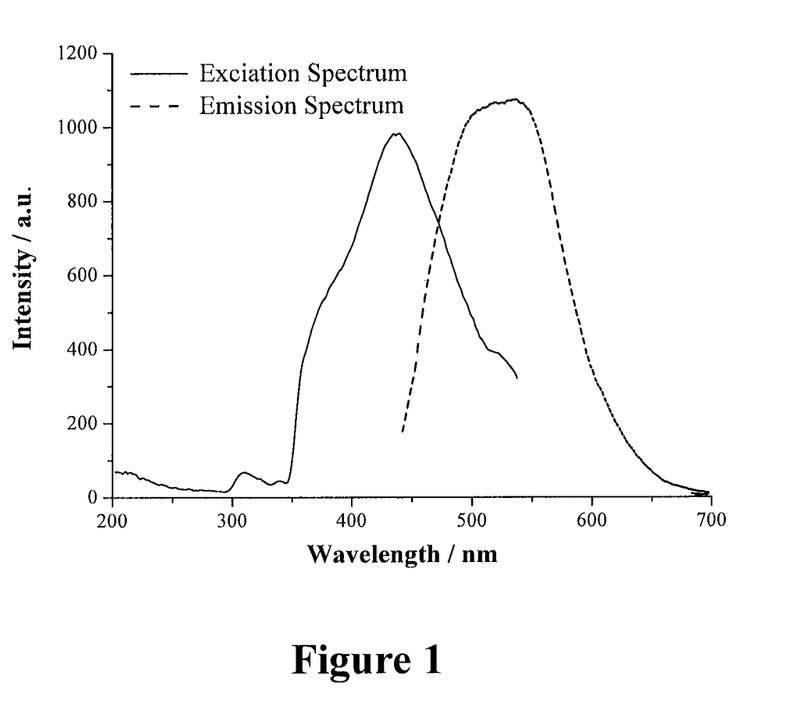
FIG. 1 shows the fluorescence spectra of $Zn(RCz-4CN-Q)_2$.

To characterize the fluorescence property of $Zn(RCz-4CN-Q)_2$, its fluorescence excitation and emission spectra of $Zn(RCz-4CN-Q)_2$ were measured with a LS-50B fluorescence spectrometer manufactured by the PerkinElmer Inc., America. Particularly, a Zn(RCz-4CN-Q)$_2$ solution in chloroform (10$^{-5}$ mol/L) was formulated, and used for measurement of liquid fluorescence spectra. FIG. 1 shows the fluorescence spectra of the present invention. As shown in FIG. 1, Zn(RCz-4CN-Q)$_2$ exhibits a major excitation band with the main peak at ~439 nm, which substantially corresponds to that of 5-position substituted zinc 8-hydroxyl quiniline (ZnQ$_2$). In addition, two weak fluorescence excitation peaks occur as shoulder peaks at ~360 nm and ~500 nm which correspond to fluorescence excitation peaks of carbazolyl group and DCDC groups, respectively (FIG. 1). As also shown in FIG. 1, the fluorescence emission spectrum of Zn(RCz-4CN-Q)$_2$ exhibits a much broad band centered at ~533 nm, and covers part of blue- and red-light areas. It can be seen that Zn(RCz-4CN-Q)$_2$ can emit a white-light by recombining three individual light excited from 5-position substituted ZnQ$_2$ group, carbazolyl group and DCDC group after it is excited.

To characterized the fluorescence quantum efficiency of Zn(RCz-4CN-Q)$_2$, solutions of quinoline sulfate (10$^{-5}$ mol/L) and Zn(RCz-4CN-Q)$_2$ (10$^{-5}$ mol/L) in chloroform were used as standard sample and test sample, respectively. The ultraviolet-visible (UV-vis) spectra of both samples were measured by a Lamdba Bio40 ultraviolet-visible light spectrometer manufactured by PerkinElmer Inc., America. The wavelength of crossing point between two spectra of the above samples in the long wavelength area was determined, which was used as the excited wavelength to record the fluorescence emission spectra of the Zn(RCz-4CN-Q)$_2$ solution in chloroform and the standard sample. Integral areas of emission spectra of both samples were determined to calculate the fluorescence quantum efficiency of Zn(RCz-4CN-Q)$_2$ according to the following Equation (1):

$$\eta_f = \eta_{fs} \times \frac{I}{I_s} \quad (1)$$

wherein, n$_f$ is the fluorescence quantum efficiency of Zn(RCz-4CN-Q)$_2$, n$_{fs}$ is the fluorescence quantum efficiency of the standard sample, I is the integral area of fluorescence emission spectrum of Zn(RCz-4CN-Q)$_2$, and I$_s$ is the integral area of fluorescence emission of the standard sample. It was calculated that the fluorescence quantum efficiency of Zn(RCz-4CN-Q)$_2$ was 0.134, which was higher than that of WOEP (<0.1).

Therefore, it can be concluded that Zn(RCz-4CN-Q)$_2$ of the present invention can realize a white-light emission with a high fluorescence quantum efficiency, which is owing to its stereo molecular structure, large steric hindrance, low molecular freedom and small probability of radiationless transition. In comparison, WOEP has a chain structure with respective main chains which cross and effect each other among molecules. Therefore, the fluorescence quantum efficiency of Zn(RCz-4CN-Q)$_2$ is higher than that of WOEP.

Photoluminescence Property

To characterize the photoluminescence (PL) property, a PL spectrum (at a ultraviolet excitation wavelength of 365 nm) and a color coordinate diagram of Zn(RCz-4CN-Q)$_2$ as a solid were measured by SPR-929D photoluminescence spectrometer manufactured by SENSING Instruments Co., Ltd., China.

Figure 2:
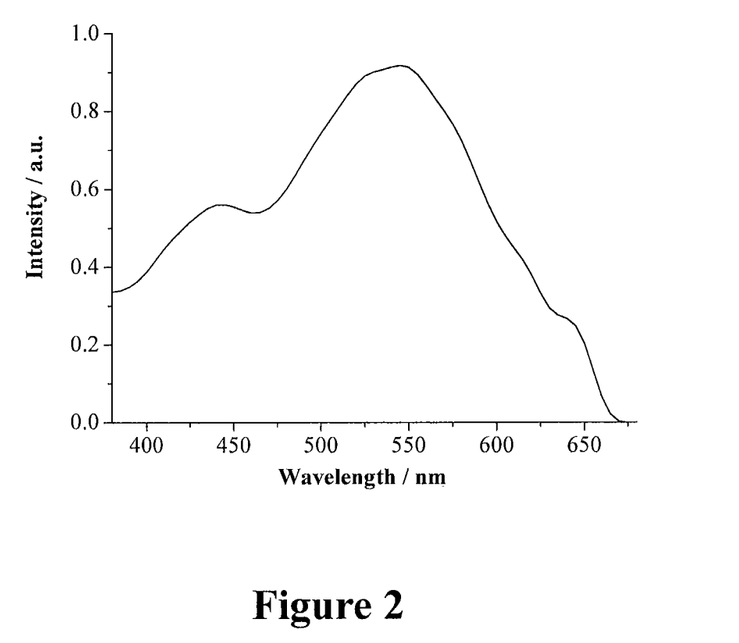
FIG. 2 shows the photoluminescence spectrum of $Zn(RCz-4CN-Q)_2$.

FIG. 2 shows the photoluminescence (PL) spectrum of Zn (RCz-4CN-Q)$_2$. As shown in FIG. 2, in the PL spectrum, Zn(RCz-4CN-Q)$_2$ exhibits a broad emission band having a band width of 182.4 nm that substantially covers the visible-light region in its PL spectrum, where a peak at 542 nm corresponds to the 5-position substituted ZnQ$_2$ group. In addition, a shoulder peak at 445 nm corresponds to blue-light emission of carbazolyl group, and a weak shoulder peak at around 630 nm corresponds to red-light emission of the red-light emitting group of DCDC group.

Figure 3:
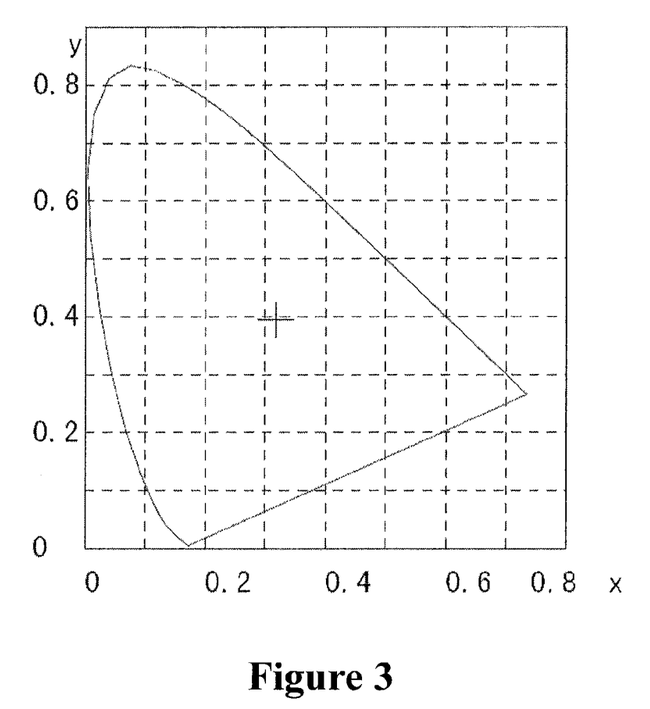
FIG. 3 shows the color coordinate chart of $Zn(RCz-4CN-Q)_2$.

FIG. 3 shows the color coordinate chart of Zn(RCz-4CN-Q)$_2$. As shown in FIG. 3, Zn(RCz-4CN-Q)$_2$ exhibits a CIE coordinate of (0.3177, 0.3946) with a coloration index of 77.7%, which just locates in the white-light area.

Therefore, it can be concluded that the Zn(RCz-4CN-Q)$_2$ of the present invention can achieve a remarkable white-light fluorescence effect, and have a broad emission band covering substantially the whole visible-light region. Therefore, the Zn(RCz-4CN-Q)$_2$ is an ideal white-light organic electroluminescent material. Moreover, the Zn(RCz-4CN-Q)$_2$ exhibit a color coordinate that is very close to the pure white light of (0.33, 0.33), and its coloration index is close to the practical white-light material of 80%.

Electrochemcal Property

To characterize the electrochemical property of Zn(RCz-4CN-Q)$_2$, the cyclic voltammetric (CV) curve was recorded on Autolab/PG STAT302 electrochemical system to determine the solution of Zn(RCz-4CN-Q)$_2$ in chloroform (10$^{-5}$ mol/L) at a scan rate of 50 mV/s, using a solution of tetrabutylammonium perchlorate (n-Bu$_4$NClO$_4$, 0.1 mol/L) in chloroform as the supporting electrolyte, and two platinum chips and a calomel electrode (222) as the working electrode, counter electrode and reference electrode, respectively.

Figure 4:
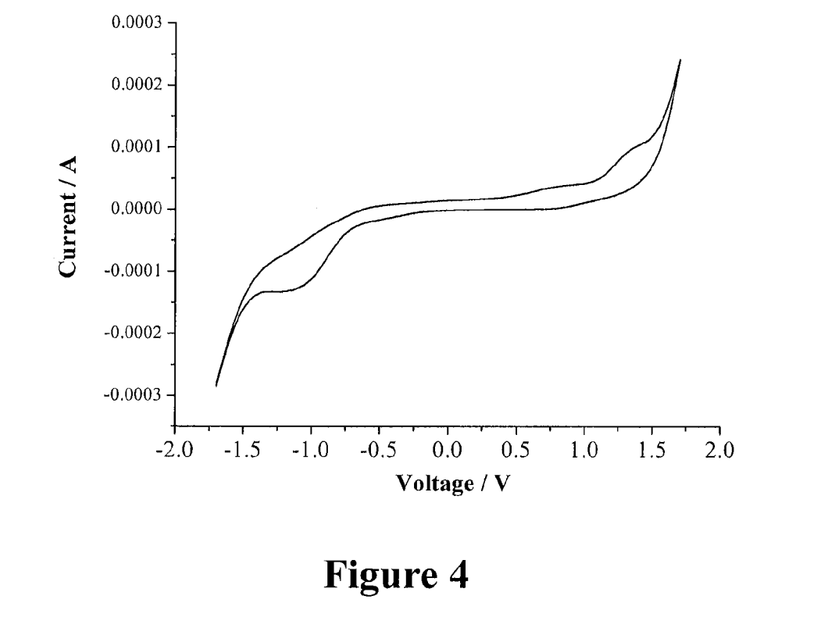
FIG. 4 shows the cyclic voltammetry curve of $Zn(RCz-4CN-Q)_2$.

FIG. 4 shows the CV curve of Zn(RCz-4CN-Q)$_2$. As shown in FIG. 4, the HOMO level, LUMO level and band gap of the Zn(RCz-4CN-Q)$_2$ are −5.84 eV, −3.25 eV and 2.59 eV, respectively. It is indicated that the Zn(RCz-4CN-Q)$_2$ possesses an ideal energy level structure, and can be used to fabricate a white-light OLED, in which energy levels of the cathode and the anode are matched effectively.

In addition, the Zn(RCz-4CN-Q)$_2$ is an organic metal complex, and has a planar molecular having strong rigidity. Therefore, in comparison with WOEP, the Zn(RCz-4CN-Q)$_2$ exhibits a better thermal stability, and has a longer device lifetime when it is used in an OLED since it can effectively avoid crystallization of film originated from Joule heat.

In summary, the present invention aims to synthesize a white-light organic electroluminescent material having combined red, green and blue light emitting groups, i.e., a compound like Zn(RCz-4CN-Q)$_2$. The material of the present invention may be used to fabricate a white-light OLED having a single light-emitting layer, and thereby resolve problems of the prior art white-light OLED.

INDUSTRIAL APPLICATION

The white-light organic electroluminescent material of the present invention can be used to realize a white-light emission by simply following an appropriate ratio during reaction, which greatly reduces the synthetic difficulty, and thereby is in favor of industrialized mass production. In addition, such a material can be used in the white-light OLED as a single light-emitting layer, which can decrease the number of layers of the white-light OLED and thereby improve the luminous efficiency, stabilize the light color, lower the turn-on voltage and simplify the fabrication process.

The invention claimed is:
1. A white-light organic electroluminescent material represented by the following Formula (I):

wherein, M represents a divalent metal ion; A represents a group containing a 8-hydroxyquinolinyl group, in which the 8-hydroxyquinolinyl group can be substituted by an alkyl, alkoxyl or amino group at 2- or 7-position; B represents a carbazolyl group; C represents a group containing a 3,3-dicyanomethylene-1-cyclohexenyl group, in which the 3,3-dicyanomethylene-1-cyclohexenyl group can be substituted by an alkyl or aromatic group at 5-position; and each of $L_1$ and $L_2$ independently represents a saturated or unsaturated linking group having 2 to 8 carbon atoms.

2. The white-light organic electroluminescent material according to claim 1, wherein M represents a divalent earth metal ion or a divalent transition metal ion.

3. The white-light organic electroluminescent material according to claim 1, wherein M represents $Zn^{2+}$.

4. The white-light organic electroluminescent material according to claim 1, wherein A represents a 8-hydroxyquinolinyl group, B represents a carbazolyl group, and C represents a 3,3-dicyanomethylene-5,5-dimethyl-cyclohexenyl group.

5. The white-light organic electroluminescent material according to claim 1, wherein $L_1$ is a linking group which links the group A containing a 8-hydroxyquinolinyl group with the carbazolyl group B, and may be a saturated or unsaturated straight linking group having 2 to 8 carbon atoms; and $L_2$ is a linking group which links the carbazolyl group B with the group C containing a 3,3-dicyanomethylene-1-cyclohexenyl group, and may be a saturated or unsaturated straight linking group having 2 to 8 carbon atoms.

6. The white-light organic electroluminescent material according to claim 1, wherein the carbazolyl group B is linked with the group A containing a 8-hydroxyquinolinyl group at its 4- or 5-position through the linking group $L_1$.

7. The white-light organic electroluminescent material according to claim 1, wherein each of the carbazolyl group B is linked with two groups C containing a 3,3-dicyanomethylene-1-cyclohexenyl group, and each of the two groups C containing a 3,3-dicyanomethylene-1-cyclohexenyl group is linked with the carbazolyl group B through the linking group $L_2$.

8. The white-light organic electroluminescent material according to claim 1, which has a structure represented by the following Formula (IX):

9. An organic light emitting diode comprising a light-emitting layer formed of the white-light organic electroluminescent material according to claim 1.

10. A method for preparing the white-light organic electroluminescent material according to claim 1, comprising the following steps:
(i) coupling a carbazolyl group B with a linking group $L_1$ to obtain a compound represented by the Formula (II);

(ii) coupling the compound represented by the Formula (II) with a group C containing a 3,3-dicyanomethylene-1-cyclohexenyl group through a linking group $L_2$ to obtain a compound represented by the Formula (III);

(iii) coupling the compound represented by the Formula (III) with a group A containing a 8-hydroxyquinolinyl group to obtain a compound represented by the Formula (IV);

(iv) chelating the compound represented by the Formula (IV) with a divalent metal ion M to obtain a compound represented by the in Formula (I);

(I)

wherein, M represents a divalent metal ion; A represents a group containing a 8-hydroxyquinolinyl group, in which the 8-hydroxyquinolinyl group can be substituted by an alkyl, alkoxyl or amino group at 2- or 7-position; B represents a carbazolyl group; C represents a group containing a 3,3-dicyanomethylene-1-cyclohexenyl group, in which the 3,3-dicyanomethylene-1-cyclohexenyl group can be substituted by an alkyl or aromatic group at 5-position; and each of $L_1$ and $L_2$ independently represents a saturated or unsaturated linking group having 2 to 8 carbon atoms.

11. The method according to claim 10, comprising the following steps:
(i-a) synthesizing N-(6-bromohexyl)-carbazole (BrRCz) from the starting material of carbazole and dibromohexane;
(i-b) preparing 3,6-diformyl-N-(6-bromohexyl)-carbazole (DFBrRCz) by reactiing BrRCz with $POCl_3$ and DMF;
(i-c) synthesizing 3,3-dicyanomethylene-5,5-dimethyl-cyclohexene (DCDC) by reacting isophorone with malononitrile; and synthesizing 3,6-bis[2-(3,3-dicyanormethylene-5,5-dimethyl-cyclohexenyl)-ethenyl]-N-(6-bromohexyl)-carbazole (BrRCz-4CN) by reacting DCM with the DFBrRCz;
(ii-a) synthesizing 3,6-bis-[2-(3,3-dicyanomethylene-5,5-dimethyl-cyclohexenyl)-ethenyl]-N-[6-(4,4,5,5-tetramethyl-1,3,2-dioxaboran-2-yl)]-hexyl]-carbazole (BRCz-4CN) by reacting the BrRCz-4CN with 2-isopropyl-4,4,5,5-tetramethyl-1,3,2-dioxa-borane;
(ii-b) synthesizing 5-{3,6-bis[2-(3,3-dicyanomethylene-5,5-dimethyl-cyclohexenyl)-ethenyl]-N-(6-hexyl)-carbazolyl}-8-hydroxyquinoline (RCz-4CN-Q) by reacting the BRCz-4CN with 5-chloro-8-hydroxyquinoline;
(iii-c) synthesizing bi{5-{3,6-bis[2-(3,3-dicyanomethylene-5,5-dimethyl-cyclohexenyl)-ethenyl]-N-(6-hexyl)-carbazolyl}-8-hydroxyquinoline}zinc (Zn(RCz-4CN-Q)$_2$) by adding zinc acetate into the RCz-4CN-Q.

12. The method according to claim 11, comprising the following steps:
(i-a) adding 1,6-dibromohexane into a solution of carbazole in THF, adding a KOH solution dropwise during stirring in a molar ratio of carbazole 1,6-dibromohexane:KOH=1:1~3:3~10 under a nitrogen atmosphere, and then reacting for 40~48 hours under reflux to synthesize the BrRCz;
(i-b) dissolving the BrRCz and DMF in 1,2-dichloroethane, adding $POCl_3$ into the resultant solution dropwise in an ice bath during stirring in a molar ratio of BrRCz:DMF:$POCl_3$=1:2~3:2~3, and after warming the resultant reaction mixture slowly, reacting for 20-24 hours under reflux to synthesize the DFBrRCz;
(i-c) adding isophorone and malononitrile into a mixed solution of glacial acetic acid, acetic anhydride, piperidine and DMF, stirring the resultant mixture at room temperature for 1~2 hours, warming up to 70~90° C. and further stirring for 1~2 hours, and then adding DFBrRCz a molar ratio of DFBrRCz:isophorone:malononitrile=1:2~8:2~8, and further reacting for 1~2 hours under 70~90° C. to synthersize the BrRCz-4CN;
(ii-a) adding N-butyllithium dropwise into a BrRCz-4CN solution in THF in a cooling bath of mixed liquid nitrogen/butanol solution under a nitrogen atmosphere in a molar ratio of BrRCz-4CN:2-isopropyl-4,4,5,5-tetramethyl-1,3,2-dioxa-borane:N-butyllithium=1:1~2:1~2, and then adding 2-isopropyl-4,4,5,5-tetramethyl-1,3,2-dioxa-borane quickly, stirring for 2~3 hours, warming up to the room temperature, and further reacting for 20-26 hours to synthesize the BRCz-4CN;
(ii-b) dissolving BRCz-4CN, Pd(PH$_3$)$_4$(O) and 5-chloro-8-hydroxyquinoline in ethylene glycol dimethyl ether in a molar ratio of BRCz-4CN:5-chloro-8-hydroxyquinoline=1:0.5~2 in the presence of the catalyst of Pd(PPH$_3$)$_4$(O) in an amount of 1/3~1/6 based on the amount of BRCz-4CN, adding equal volume based on the volume of ethylene glycol dimethyl ether of Na$_2$CO$_3$ aqueous solution in a concentration of 2 mol/L, and reacting for 20~26 hours under reflux to synthesize the RCz-4CN-Q;
(iii-c) dissolving RCz-4CN-Q and zinc acetate in anhydrous methanol in a molar ratio of 1-3:1, and reacting for 3~5 hours under reflux to synthesize the Zn(RCz-4CN-Q)$_2$.

13. The method according to claim 12, wherein in the step (I-a), the amount of THF as solvent makes up 25"35% of the total reaction system, in the step (i-b) the amount of 1,2-dichloroethane as solvent makes up 80-90% of the total reaction system, in the step (ii-a) the amount of THF as solvent makes up 90-95% of the total reaction system, and in the step (ii-b) the amount of ethylene glycol dimethyl ether as solvent makes up 40-60% of the total reaction system.

14. The white-light organic electroluminescent material according to claim 2, wherein A represents a 8-hydroxyquinolinyl group, B represents a carbazolyl group, and C represents a 3,3-dicyanomethylene-5,5-dimethyl-cyclohexenyl group.

15. The white-light organic electroluminescent material according to claim 3, wherein A represents a 8-hydroxyquinolinyl group, B represents a carbazolyl group, and C represents a 3,3-dicyanomethylene-5,5-dimethyl-cyclohexenyl group.

* * * * *